(12) United States Patent
Felts et al.

(10) Patent No.: US 8,439,981 B2
(45) Date of Patent: May 14, 2013

(54) SOLUBLE SOLID HAIR COLORING ARTICLE

(75) Inventors: Timothy James Felts, Hamilton, OH (US); Guiru Zhang, Lebanon, OH (US); Jorge Max Sunkel, Cincinnati, OH (US); Bryan Patrick Murphy, Loveland, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 13/478,719

(22) Filed: May 23, 2012

(65) Prior Publication Data

US 2012/0301412 A1   Nov. 29, 2012

Related U.S. Application Data

(60) Provisional application No. 61/490,794, filed on May 27, 2011.

(51) Int. Cl.
*A61Q 5/10* (2006.01)

(52) U.S. Cl.
USPC .................. 8/405; 8/477; 8/526; 8/552; 8/658

(58) Field of Classification Search .............. 8/405, 477, 8/526, 552, 658
See application file for complete search history.

(56) References Cited

U.S. PATENT DOCUMENTS

| | | | |
|---|---|---|---|
| 2,356,168 A | 8/1944 | Mabley |
| 2,396,278 A | 3/1946 | Lind |
| 2,438,091 A | 3/1948 | Lynch |
| 2,486,921 A | 11/1949 | Byerly |
| 2,486,922 A | 11/1949 | Strain |
| 2,528,378 A | 10/1950 | Mannheimer |
| 2,658,072 A | 11/1953 | Kosmin |
| 2,694,668 A | 11/1954 | Fricke |
| 2,809,971 A | 10/1957 | Bernstein |
| 3,152,046 A | 10/1964 | Kapral |
| 3,236,733 A | 2/1966 | Karsten |
| 3,321,425 A | 5/1967 | Blau |
| 3,332,880 A | 7/1967 | Kessler |
| 3,426,440 A | 2/1969 | Shen |
| 3,489,688 A | 1/1970 | Pospischil |
| 3,653,383 A | 4/1972 | Wise |
| 3,753,196 A | 8/1973 | Kurtz |
| 3,761,418 A | 9/1973 | Parran, Jr. |

(Continued)

FOREIGN PATENT DOCUMENTS

| | | |
|---|---|---|
| CN | 1138091 A | 12/1996 |
| CN | 1219388 A | 6/1999 |

(Continued)

OTHER PUBLICATIONS

U.S. Appl. No. 13/597,539, Aug. 29, 2012, Glenn, Jr. et al.

(Continued)

*Primary Examiner* — Eisa Elhilo
(74) *Attorney, Agent, or Firm* — James T. Fondriest

(57) ABSTRACT

A soluble solid hair coloring article having anionic direct dye and one or more soluble porous solids containing nonionic surfactant, anionic surfactant, or a mixture thereof, such that the soluble porous solid has a density of from about 0.03 g/cm3 to about 0.15 g/cm3; and methods of applying the soluble solid hair coloring article to hair.

21 Claims, 2 Drawing Sheets

U.S. PATENT DOCUMENTS

| | | |
|---|---|---|
| 3,929,678 A | 12/1975 | Laughlin |
| 3,967,921 A | 7/1976 | Haberli |
| 4,020,156 A | 4/1977 | Murray |
| 4,051,081 A | 9/1977 | Jabs |
| 4,089,945 A | 5/1978 | Brinkman |
| 4,149,551 A | 4/1979 | Benjamin et al. |
| 4,196,190 A | 4/1980 | Gehman |
| 4,197,865 A | 4/1980 | Jacquet |
| 4,206,196 A | 6/1980 | Davis |
| 4,217,914 A | 8/1980 | Jacquet |
| 4,272,511 A | 6/1981 | Papantoniou |
| 4,323,683 A | 4/1982 | Bolich, Jr. |
| 4,345,080 A | 8/1982 | Bolich, Jr. |
| 4,379,753 A | 4/1983 | Bolich, Jr. |
| 4,381,919 A | 5/1983 | Jacquet |
| 4,422,853 A | 12/1983 | Jacquet |
| 4,470,982 A | 9/1984 | Winkler |
| 4,507,280 A | 3/1985 | Pohl |
| 4,529,586 A | 7/1985 | De Marco |
| 4,565,647 A | 1/1986 | Llenado |
| 4,663,158 A | 5/1987 | Wolfram |
| 4,710,374 A | 12/1987 | Grollier |
| 4,822,613 A | 4/1989 | Rodero |
| 4,885,107 A | 12/1989 | Wetzel |
| 4,976,953 A | 12/1990 | Orr |
| 4,990,280 A | 2/1991 | Thorengaard |
| 5,055,384 A | 10/1991 | Kuhnert |
| 5,061,481 A | 10/1991 | Suzuki |
| 5,062,889 A | 11/1991 | Hohl |
| 5,094,853 A | 3/1992 | Hagarty |
| 5,100,657 A | 3/1992 | Ansher-Jackson |
| 5,100,658 A | 3/1992 | Bolich, Jr. |
| 5,104,646 A | 4/1992 | Bolich, Jr. |
| 5,106,609 A | 4/1992 | Bolich, Jr. |
| 5,166,276 A | 11/1992 | Hayama |
| 5,220,033 A | 6/1993 | Kamei |
| 5,261,426 A | 11/1993 | Kellett et al. |
| 5,280,079 A | 1/1994 | Allen |
| RE34,584 E | 4/1994 | Grote |
| 5,391,368 A | 2/1995 | Gerstein |
| 5,409,703 A | 4/1995 | McAnalley |
| 5,429,628 A | 7/1995 | Trinh |
| 5,457,895 A | 10/1995 | Thompson |
| 5,476,597 A | 12/1995 | Sakata |
| 5,580,481 A | 12/1996 | Sakata |
| 5,582,786 A | 12/1996 | Brunskill |
| 5,660,845 A | 8/1997 | Trinh |
| 5,672,576 A | 9/1997 | Behrens |
| 5,674,478 A | 10/1997 | Dodd |
| 5,750,122 A | 5/1998 | Evans |
| 5,769,901 A | 6/1998 | Fishman |
| 5,780,047 A | 7/1998 | Kamiya |
| 5,879,414 A * | 3/1999 | Milazzo ............................ 8/433 |
| 5,955,419 A | 9/1999 | Barket, Jr. |
| 5,976,454 A | 11/1999 | Sterzel et al. |
| 6,010,719 A | 1/2000 | Remon |
| 6,106,849 A | 8/2000 | Malkan |
| 6,177,391 B1 | 1/2001 | Zafar |
| 6,200,949 B1 | 3/2001 | Reijmer |
| 6,365,142 B1 | 4/2002 | Tamura |
| 6,458,754 B1 | 10/2002 | Velazquez |
| 6,503,521 B1 | 1/2003 | Atis |
| 6,802,295 B2 | 10/2004 | Fox |
| 6,808,375 B2 | 10/2004 | Klotzer |
| 6,825,161 B2 | 11/2004 | Shefer et al. |
| 6,831,046 B2 | 12/2004 | Carew et al. |
| 6,846,784 B2 | 1/2005 | Engel |
| 6,943,200 B1 | 9/2005 | Corrand |
| 7,015,181 B2 | 3/2006 | Lambino |
| 7,225,920 B2 | 6/2007 | Hoeffkes |
| 7,285,520 B2 | 10/2007 | Krzysik |
| 7,387,787 B2 | 6/2008 | Fox |
| 7,611,545 B2 | 11/2009 | Guerin et al. |
| 7,846,462 B2 | 12/2010 | Spadini et al. |
| 7,901,696 B2 | 3/2011 | Eknoian |
| 8,197,830 B2 | 6/2012 | Helfman et al. |
| 2002/0064510 A1 | 5/2002 | Dalrymple |
| 2002/0077264 A1 | 6/2002 | Roberts |
| 2002/0081930 A1 | 6/2002 | Jackson |
| 2002/0098994 A1 | 7/2002 | Zafar |
| 2002/0099109 A1 | 7/2002 | Dufton |
| 2002/0177621 A1 | 11/2002 | Hanada |
| 2002/0187181 A1 | 12/2002 | Godbey |
| 2003/0032573 A1 | 2/2003 | Tanner |
| 2003/0033678 A1 | 2/2003 | Schulze zur Wiesche |
| 2003/0045441 A1 | 3/2003 | Hsu |
| 2003/0069154 A1 | 4/2003 | Hsu |
| 2003/0080150 A1 | 5/2003 | Cowan |
| 2003/0099691 A1 | 5/2003 | Lydzinski |
| 2003/0099692 A1 | 5/2003 | Lydzinski |
| 2003/0180242 A1 | 9/2003 | Eccard |
| 2003/0186826 A1 | 10/2003 | Eccard |
| 2003/0194416 A1 | 10/2003 | Shefer |
| 2003/0199412 A1 | 10/2003 | Gupta |
| 2003/0207776 A1 | 11/2003 | Shefer |
| 2003/0215522 A1 | 11/2003 | Johnson |
| 2003/0232183 A1 | 12/2003 | Dufton |
| 2004/0029762 A1 | 2/2004 | Hensley |
| 2004/0048759 A1 | 3/2004 | Ribble |
| 2004/0053808 A1 | 3/2004 | Raehse |
| 2004/0071742 A1 | 4/2004 | Popplewell |
| 2004/0071755 A1 | 4/2004 | Fox |
| 2004/0108615 A1 | 6/2004 | Foley |
| 2004/0110656 A1 | 6/2004 | Casey |
| 2004/0126585 A1 | 7/2004 | Kerins |
| 2004/0175404 A1 | 9/2004 | Shefer |
| 2004/0202632 A1 | 10/2004 | Gott |
| 2004/0206270 A1 | 10/2004 | Vanmaele |
| 2004/0242772 A1 | 12/2004 | Huth |
| 2005/0069575 A1 | 3/2005 | Fox |
| 2005/0136780 A1 | 6/2005 | Clark |
| 2005/0137272 A1 | 6/2005 | Gaserod |
| 2005/0202992 A1 | 9/2005 | Grandio Portabales |
| 2005/0220745 A1 | 10/2005 | Lu |
| 2005/0232954 A1 | 10/2005 | Yoshinari |
| 2005/0272836 A1 | 12/2005 | Yaginuma |
| 2005/0287106 A1 | 12/2005 | Legendre |
| 2006/0002880 A1 | 1/2006 | Peffly |
| 2006/0052263 A1 | 3/2006 | Roreger |
| 2006/0228319 A1 | 10/2006 | Vona |
| 2007/0028939 A1 | 2/2007 | Mareri |
| 2007/0039103 A1 | 2/2007 | Godfrey |
| 2007/0148102 A1 | 6/2007 | Kalbfleisch |
| 2007/0149435 A1 | 6/2007 | Koenig |
| 2007/0225388 A1 | 9/2007 | Cooper et al. |
| 2008/0035174 A1 | 2/2008 | Aubrun-Sonneville |
| 2008/0083420 A1 | 4/2008 | Glenn et al. |
| 2008/0090939 A1 | 4/2008 | Netravali |
| 2008/0131695 A1 | 6/2008 | Aouad |
| 2008/0138492 A1 | 6/2008 | Cingotti |
| 2008/0152894 A1 | 6/2008 | Beihoffer |
| 2008/0215023 A1 | 9/2008 | Scavone |
| 2008/0293839 A1 | 11/2008 | Stobby |
| 2009/0232873 A1 | 9/2009 | Glenn, Jr. |
| 2009/0263342 A1 | 10/2009 | Glenn, Jr. |
| 2010/0167971 A1 | 7/2010 | Glenn, Jr. |
| 2010/0173817 A1 | 7/2010 | Glenn, Jr. |
| 2010/0179083 A1 | 7/2010 | Glenn, Jr. |
| 2010/0279905 A1 | 11/2010 | Glenn, Jr. |
| 2010/0286011 A1 | 11/2010 | Glenn, Jr. |
| 2010/0291165 A1 | 11/2010 | Glenn, Jr. |
| 2010/0298188 A1 | 11/2010 | Glenn, Jr. |
| 2011/0023240 A1 | 2/2011 | Fossum |
| 2011/0027328 A1 | 2/2011 | Baig et al. |
| 2011/0028373 A1 | 2/2011 | Fossum |
| 2011/0028374 A1 | 2/2011 | Fossum |
| 2011/0182956 A1 | 7/2011 | Glenn, Jr. |
| 2011/0189246 A1 | 8/2011 | Glenn, Jr. |
| 2011/0189247 A1 | 8/2011 | Glenn, Jr. |
| 2011/0195098 A1 | 8/2011 | Glenn, Jr. |
| 2012/0021026 A1 | 1/2012 | Glenn, Jr. |
| 2012/0270029 A1 | 10/2012 | Glenn, Jr. |
| 2012/0289451 A1 | 11/2012 | Glenn, Jr. |
| 2012/0297556 A1 | 11/2012 | Felts |

FOREIGN PATENT DOCUMENTS

| | | | |
|---|---|---|---|
| CN | 1268558 | A | 10/2000 |
| CN | 1357613 | A | 7/2002 |
| CN | 1530431 | A | 9/2004 |
| CN | 1583991 | A | 2/2005 |
| DE | 19607851 | A1 | 9/1997 |
| DE | 10331767 | A1 | 2/2005 |
| EP | 609808 | A1 | 8/1994 |
| EP | 0858828 | A1 | 8/1998 |
| EP | 1160311 | B1 | 12/2001 |
| EP | 1217987 | B1 | 12/2004 |
| EP | 1958532 | A2 | 8/2008 |
| EP | 2085434 | A1 | 8/2009 |
| FR | 2871685 | A | 12/2005 |
| FR | 2886845 | A | 12/2006 |
| GB | 2235204 | A | 2/1991 |
| GB | 2355008 | A | 4/2001 |
| JP | 58021608 | A | 2/1983 |
| JP | 58216109 | A | 12/1983 |
| JP | 62072609 | A | 4/1987 |
| JP | 62072610 | A | 4/1987 |
| JP | 1313418 | A | 12/1989 |
| JP | 5344873 | A | 12/1993 |
| JP | 6017083 | A | 1/1994 |
| JP | 7089852 | A | 4/1995 |
| JP | 8325133 | A | 12/1996 |
| JP | 10251371 | A | 9/1998 |
| JP | 2003073700 | A | 3/2003 |
| JP | 2003082397 | A | 3/2003 |
| JP | 2004345983 | A | 12/2004 |
| JP | 2005171063 | A | 6/2005 |
| JP | 2007197540 | A | 8/2007 |
| JP | 2007091954 | A | 12/2007 |
| KR | 20020003442 | | 1/2002 |
| WO | WO 1995014495 | A1 | 6/1995 |
| WO | WO 2001/024770 | A1 | 4/2001 |
| WO | WO 2004/032859 | A | 4/2004 |
| WO | WO 2004/041991 | A1 | 5/2004 |
| WO | WO 2005/003423 | A1 | 1/2005 |
| WO | WO 2007033598 | A1 | 3/2007 |
| WO | WO 2007/093558 | A2 | 8/2007 |
| WO | WO 2009019571 | | 2/2009 |

OTHER PUBLICATIONS

U.S. Appl. No. 13/478,742, May 23, 2012, Felts et al.
P&G Case 11200M ISR dated May 6, 2011, PCT/US2009/067130, 5 pages.
P&G Case 11201M ISR dated May 4, 2011, PCT/US2009/067088, 5 pages.
P&G Case 11201M ISR dated Jul. 19, 2011, PCT/US2009/067088, 7 pages.
P&G Case 11202M3 ISR dated May 9, 2011, PCT/US2009/067132, 5 pages.
P&G Case 11202M2 ISR dated Jul. 20, 2011, PCT/US2009/067131, 5 pages.
P&G Case 11202M ISR dated Apr. 29, 2011, PCT/US2009/067089, 5 pages.
P&G Case 10997M ISR dated Jul. 15, 2009, PCT/IB2009/050388, 8 pages.
P&G Case 11037M ISR dated Aug. 17, 2009, PCT/US2009/040739, 6 pages.
P&G Case 11037M ISR dated Nov. 4, 2009, PCT/US2009/040739, 10 pages.
P&G Case 11199M ISR dated Dec. 15, 2011, PCT/US2009/067087, 5 pages.
P&G Case 11203M ISR dated Jul. 19, 2011, PCT/US2009/067133, 4 pages.
P&G Case 11200M ISR dated Jul. 19, 2011, PCT/US2009/067130, 7 pages.
P&G Case 11494M ISR dated Apr. 27, 2011, PCT/US2010/059365, 5 pages.
P&G Case 11495M ISR dated Apr. 27, 2011, PCT/US2010/059455, 5 pages.
P&G Case 12068M ISR dated Jul. 20, 2012, PCT/US2012/032253, 5 pages.
P&G Case 11523M ISR dated Apr. 27, 2011, PCT/US2010/059359, 5 pages.
T. Hildebrand, P. Rüegsegger. "Quantification of bone microarchitecture with the structure model index." Computer Methods in Biomechanics and Biomedical Engineering 1997; 1:15-23.
Vesterby, A.; Star volume in bone research. A histomorphometric analysis of trabecular bone structure using vertical sections; Anat Rec.; Feb. 1993; 235(2):325-334.
C. D. Vaughan. Solubility, Effects in Product, Package, Penetration and Preservation, Cosmetics and Toiletries, vol. 103, October 1988.
*Encyclopedia of Polymer Science and Engineering,* vol. 15, 2d ed., pp. 204-308, John Wiley & Sons, Inc. (1989).
Anonymous: "P8136 Poly(vinyl alcohol)" Internet article, [Online] XP002538935 Retrieved from the Internet: URL:http://www.sigmaaldrich.com/catalog/ProductDetail.do?D7=O&N25=SEARCH_CONCAT_PNO%7CBRAND_KEY&N4=P8136%7CSIAL&N25=0&QS=0N&F=Spec> [retrieved on 2009-07-28].
All Office Actions, U.S. Appl. No. 12/424,812, (May 24, 2012).
All Office Actions, U.S. Appl. No. 12/633,228, (Sep. 5, 2012).
All Office Actions, U.S. Appl. No. 12/633,257, (Aug, 29, 2012).
All Office Actions, U.S. Appl. No. 12/633,301, (Sep. 5, 2012).
All Office Actions, U.S. Appl. No. 12/633,550, (Sep. 28, 2012).
All Office Actions, U.S. Appl. No. 12/633,335, (Aug. 13, 2012).
All Office Actions, U.S. Appl. No. 12/633,415, (Aug. 13, 2012).
All Office Actions, U.S. Appl. No. 12/633,572, (Dec. 12, 2012).
All Office Actions, U.S. Appl. No. 12/361,634, (Sep. 14, 2012).
All Office Actions, U.S. Appl. No. 12/962,846, (Sep. 17, 2012).
All Office Actions, U.S. Appl. No. 12/962,873, (Oct. 3, 2012).
All Office Actions, U.S. Appl. No. 12/962,888, (Dec. 12, 2012).
All Office Actions, U.S. Appl. No. 12/962,905, (Oct. 9, 2012).
All Office Actions, U.S. Appl. No. 13/173,639, Nov. 14, 2012).
All Office Actions, U.S. Appl. No. 13/440,475, No dates.

* cited by examiner

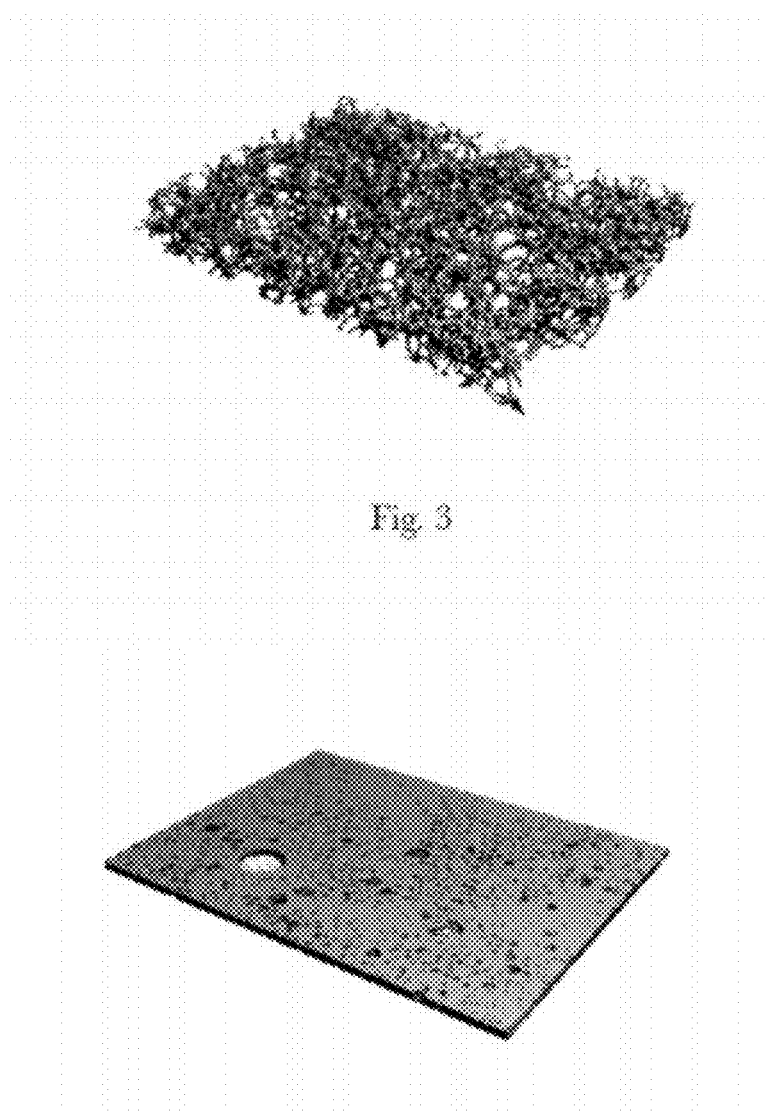
Fig. 3
Fig. 4
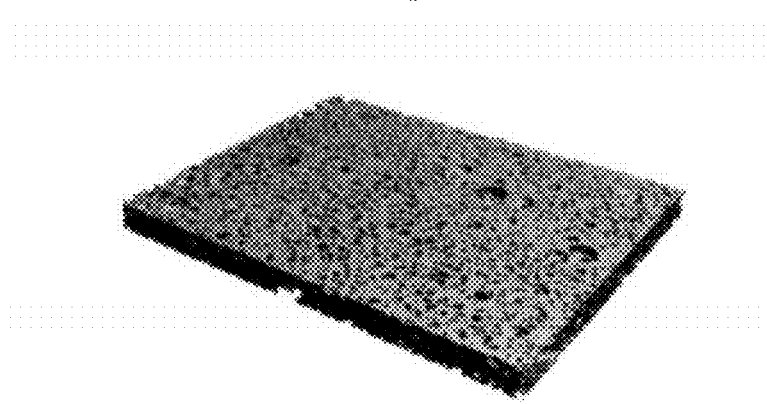
Fig. 5

SOLUBLE SOLID HAIR COLORING ARTICLE

CROSS REFERENCE TO RELATED APPLICATION

This application claims the benefit of U.S. Provisional Application Ser. No. 61/490,794 filed May 27, 2011.

FIELD OF THE INVENTION

The present invention relates to a soluble solid hair coloring article utilizing anionic direct dyes in conjunction with, and/or incorporated into, a soluble substrate.

BACKGROUND OF THE INVENTION

The majority of personal care products in the market today are sold as liquid products. While widely used, liquid products have disadvantages in terms of packaging, storage, transportation, and convenience of use. Liquid personal care products typically are sold in bottles which add significant cost as well as packaging waste, much of which ends up in land-fills.

Solid hair dyes are known, but generally discussed in terms of powdered oxidative dyes that are mixed with a developer solution before application onto the hair. Such products still require a traditional kit of dye and developer compositions.

Solid personal care products in the form of dissolvable foams are also known. See WO 2010/077650. U.S. Pat. No. 7,225,920 B2 discusses a bleaching composition sealed into a water soluble pouch that is then dissolved in water. EP 1745769 B1 discusses a liquid that is foamed and then dries to form a hair coloring product. U.S. Pat. No. 5,879,414 A discusses a hydrous solid wash resistant hair colorant stick composition. US 2003/0033678 discusses a shaped body useful for forming cosmetic preparation such as hair coloring preparations. U.S. Pat. No. 5,769,901 discusses a powdered hair dye including an oxidative dye component, an oxidizing component and a thickening component.

There still exists a need to provide a soluble solid hair coloring product that is stable and delivers desired hair color results. It has surprisingly been found that the selection of anionic surfactant in the porous solid must be compatible with the desired direct dyes in order to provide a hair colorant. As direct dyes are essentially salts, it is not obvious as to how such direct dyes will affect formulated product and stability of the formulated product. A balance must be found between delivering the desired color results and producing a stable product that is robust in view of the salt levels present.

It is an object of the present invention to provide a soluble hair coloring product from an open-celled porous solid that can be conveniently and quickly dissolved in the palm of the consumer to reconstitute a liquid product for ease of application to hair while providing sufficient topical delivery of active agents for partial or whole head hair applications with similar performance as today's liquid products. It is a further object of the present invention to provide such a product that can be produced by physical aeration followed by subsequent drying. It is an even further object of the present invention to provide such a product with desirable softness and flexibility.

SUMMARY OF THE INVENTION

The present invention relates to a soluble solid hair coloring article comprising: from about 0.4 to about 2.0 grams of anionic direct dye; one or more soluble porous solids comprising: from about 10% to about 50% polymeric structurant; from about 1% to about 30% plasticizer; and from about 2% to about 75% nonionic surfactant, an anionic surfactant, or a mixture thereof; wherein the density of the one or more soluble porous solids is from about 0.03 g/cm3 to about 0.15 g/cm3.

The present invention further relates to a method of coloring hair comprising the steps of: exposing a soluble solid hair coloring article comprising anionic direct dye and one or more soluble porous solids to a solvent, such that the soluble solid hair coloring article dissolves to form a hair coloring solution, wherein the ratio of anionic direct dye to hair is from 2:1 to 5:1; and applying the hair coloring solution to hair.

BRIEF DESCRIPTION OF THE DRAWINGS

FIG. 3 is a micro computed tomography system image of a soluble porous solid having a density of 0.07 grams/cm$^3$ (with 90 seconds of mixing);

FIG. 4 is a micro computed tomography system image of a comparative example in Table 10 and 11 having a density of 0.21 grams/cm$^3$ with 30 seconds mixing;

FIG. 5 is a micro computed tomography system image of a comparative example in Table 10 and 11 having a density of 0.16 grams/cm$^3$ with 60 seconds mixing.

DETAILED DESCRIPTION OF THE INVENTION

Figure 1:
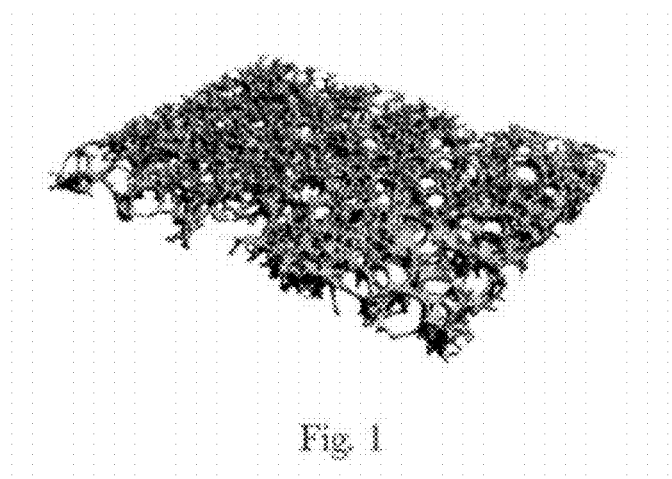
FIG. 1 is a micro computed tomography system image of a soluble porous solid having a density of 0.12 grams/cm$^3$ (with 30 seconds mixing)

In all embodiments of the present invention, all percentages are by weight of the total composition, unless specifically stated otherwise. All ratios are weight ratios, unless specifically stated otherwise. All ranges are inclusive and combinable. The number of significant digits conveys neither a limitation on the indicated amounts nor on the accuracy of the measurements. All numerical amounts are understood to be modified by the word "about" unless otherwise specifically indicated. Unless otherwise indicated, all measurements are understood to be made at 25° C. and at ambient conditions, where "ambient conditions" means conditions under about one atmosphere of pressure and at about 50% relative humidity. All such weights as they pertain to listed ingredients are based on the active level and do not include carriers or by-products that may be included in commercially available materials, unless otherwise specified.

DEFINITIONS

The term "porous solid" as used herein, unless otherwise specified, refers to a solid, interconnected, polymer-containing matrix that defines a network of spaces or cells that contain a gas, typically a gas such as air (open-celled structure), where the network of spaces or cells is substantially interconnected.

It is believed that such porous solids comprising predominantly open-cells enable rapid water flux inside the structure, exposing a multiplicity of additional solid surface area for vastly increased dissolution rates. This is in contrast to substrates comprised of predominantly closed cells, whereby the vast majority of the interior cellular surfaces are not rapidly exposed to the water upon wetting and with dissolution progressing mainly through surface erosion, which results in slower dissolution.

It has been found that a soluble solid hair coloring article can be prepared that can be conveniently and quickly dissolved by a consumer in their hand to form a liquid hair coloring product for ease of application to hair while providing sufficient topical delivery of direct dye for partial hair applications (such as root touch up application or highlighting/low-lighting applications) or whole head hair applications with similar performance as conventional liquid hair colorant products. It has also been found that the soluble solid hair coloring articles can be produced in an economical manner by physical aeration followed by subsequent drying.

The desired balance between forming a predominantly interconnected, open-celled structure and direct dye deposition properties after reconstitution has been achieved by employing nonionic surfactant, anionic surfactant, or combinations of thereof that enable foam generation under the high energy processing conditions employed during aeration to produce the structure of the soluble porous solid.

The selection of surfactant for use in the soluble solid hair coloring article is also impacted by the presence of materials known as direct dyes, which often carry a charge that may interact adversely to surfactants carrying an opposite charge (e.g., anionic or acidic direct dyes with cationic surfactant).

Soluble Solid Hair Coloring Article

Direct Dyes

The soluble solid hair coloring article comprises at least one direct dye suitable for delivering shade modification or highlights. Depending upon the desired resulting hair color, multiple direct dyes may be combined to achieve the desired resulting hair color.

The direct dye may be contained by the porous solid in the sense that the porous solid forms a holding container for the direct dye. Suitable holding container structures include an envelope, pouch or sandwich structure. The "envelope" and "pouch" structures may be from a single soluble porous solid that is folded to receive the direct dye and any other desired components. As used herein, "sandwich" structure refers to utilizing two soluble porous solids that at least partially overlap such that where the two soluble porous solids are contiguous, the direct dye and any other desired components are located between the two soluble porous solids. Alternatively, the direct dye may be incorporated as part of the processing mixture used to form the soluble porous solid.

The amount of direct dye should be selected to give the desired amount delivered to the hair to be dyed. As used herein "hair" encompasses keratin fibers such as human hair, wigs, extensions, fur and the like. If a whole head hair application is desired, then amounts of the direct dye should be selected to give the delivery of 1.0 to 1.5 wt % by weight of the hair of direct dye to the whole head of hair, or approximately 10 to 15 mg of direct dye per gram of hair. The amount of hair on a whole head may be from 5 g to 200 g and depends upon the length of the hair. The average amount of hair on a whole head may be from about 40 g to about 60 g. If a partial head hair application, such as highlighting or low lighting, is desired, then the amounts of the direct dye should be selected to reflect the lower weight of hair to which the direct dye will be applied.

In one embodiment, the ratio of direct dye to hair is from 3:1 to 5:1, such as 4:1. The amount of direct dye in the soluble hair coloring article may be from about 0.4 to about 2.0 grams.

The direct dyes may be anionic, nonionic, or zwitterionic in nature.

Colors resulting from the direct dyes may be influenced or controlled by the selection of and mixing of individual dyes to achieve the targeted end color. Direct dyes may be selected from red, blue and yellow color categories. The mixing of these direct dyes may be used to achieve the hair color desired. One example is to mix a red direct dye, a blue direct dye and a yellow direct dye in a 1:1:1 mass ratio.

The following is a list of exemplary dyes:

| Anionic Direct Dyes (Acidic Direct Dyes) | | |
|---|---|---|
| Name | Color | CAS number |
| 7-(2',4'-dimethyl-5'-sulfophenylazo)-5-sulfo-8-hydroxynaphthalene (Ponceau SX, FD&C red 4) | red | 4548-53-2 |
| Acid Red 4 | red | 5858-39-9 |
| Acid Red 33 | red | 3567-66-6 |
| Acid Violet 43 | violet | 4430-18-6 |
| Acid Yellow 1 | yellow | 846-70-8 |
| Acid Yellow 23 | yellow | 1934-21-0 |
| sodium salt of mixture of mono- & disulfonic acids (mainly the latter) of quinophthlanone or 2-quinolylindandione | yellow | NA |
| Acid Orange 3 | orange | 6373-74-6 |
| Acid Orange 7 | orange | 633-96-5 |
| Acid Blue 9 | blue | 3844-45-9 |
| Acid Blue 25 | blue | 6408-78-2 |
| Acid Blue 62 | blue | 4368-56-3 |
| Acid Blue 199 | blue | 12219-28-2 |
| Pigment Blue 15 | blue | 147-14-8 |
| 1-(3'-nitro-5'-sulfo-6'-oxophenylazo)-oxo-naphthalene chromium complex | brown | 6370-15-6 |
| Acid Black 1 | black | 1064-48-8 |
| Acid Black 52 | black | 5610-64-0 |
| Acid Black 132 | black | 12219-02-2 |

| Nonionic Direct Dyes | | |
|---|---|---|
| Disperse Red 17 | red | 3179-89-3 |
| Picramic Acid | red | 96-91-3 |
| HC Red No. 13 | red | 94158-13-1 |
| HC Red No. 7 | red | 24905-87-1 |
| HC Red No. 1 | red | 2784-89-6 |
| 2-chloro-5-nitro-N-hydroxyethyl-p-phenylenediamine | red | 50610-28-1 |
| HC Red No. 3 | red | 2871-01-4 |
| 4-amino-3-nitrophenol | red | 610-81-1 |
| 3-nitro-p-hydroxyethylaminophenol | red | 65235-31-6 |
| 2-amino-3-nitrophenol | red | 603-85-0 |
| HC Red No. 10 | red | 95576-89-9 |
| HC Red No. 11 | red | 95576-92-4 |
| 2-hydroxyethyl picramic acid | red | 99610-72-7 |
| 2-chloro-6-ethylamino-4-nitrophenol | red | 131657-78-8 |
| 6-nitro-2,5-pyridinediamine | red | 69825-83-8 |
| 2-amino-6-chloro-4-nitrophenol | red | 6358-09-4 |
| 4-hydroxypropylamino-3-nitrophenol | red | 92952-81-3 |
| N-(2-nitro-4-aminophenyl)-allylamine | red | 160219-76-1 |
| Disperse Red 15 | red | 116-85-8 |
| HC Red No. 9 | red | 56330-88-2 |
| Cochenille (a.k.a. carminic acid, natural red 4, Cochineal Red PWD) | red | 1260-17-9 |
| HC Red No. 14 | red | 99788-75-7 |
| 4-nitro-o-phenylenediamine | orange-red | 99-56-9 |
| 2-nitro-p-phenylenediamine | orange-red | 5307-14-2 |
| 2-hydroxy-1,4-naphthoquinone (a.k.a. Henna, Lawsone) | reddish brown | 83-72-7 |
| Henna Red (a.k.a. Henna) | reddish brown | 253167-73-6 |
| Disperse Violet 4 | violet | 1220-94-6 |
| 1,4-bis-(2'-hydroxyethylamino)-2-nitrobenzene | violet | 84041-77-0 |

-continued

| Nonionic Direct Dyes | | |
|---|---|---|
| HC Violet No. 1 | violet | 82576-75-8 |
| Disperse Violet 1 | violet | 128-95-0 |
| HC Violet No. 2 | violet | 104226-19-9 |
| HC Yellow No. 5 | yellow | 56932-44-6 |
| HC Yellow No. 4 | yellow | 59820-43-8 |
| HC Yellow No. 2 | yellow | 4926-55-0 |
| 3-methylamino-4-nitrophenoxyethanol | yellow | 59820-63-2 |
| 6-nitro-o-toluidine | yellow | 570-24-1 |
| 2-nitro-5-glycerylmethylaniline | yellow | 80062-31-3 |
| HC Yellow No. 11 | yellow | 73388-54-2 |
| HC Yellow No. 9 | yellow | 86419-69-4 |
| 4-nitrophenyl aminoethylurea | yellow | 27080-42-8 |
| HC Yellow No. 6 | yellow | 104333-00-8 |
| hydroxyethyl-2-nitro-p-toluidine | yellow | 100418-33-5 |
| HC Yellow No. 12 | yellow | 59320-13-7 |
| HC Yellow No. 7 | yellow | 104226-21-3 |
| HC Yellow No. 10 | yellow | 109023-83-8 |
| N-ethyl-3-nitro PABA | yellow | 2788-74-1 |
| HC Yellow No. 13 | yellow | 10442-83-8 |
| HC Yellow No. 15 | yellow | 138377-66-9 |
| HC Yellow No. 14 | yellow | 90349-40-9 |
| 2,6-diamino-3-((pyridine-3-yl)azo)pyridine | yellow | 28365-08-4 |
| HC Orange No. 1 | orange | 54381-08-7 |
| 2-hydroxyethylamino-5-nitroanisole | orange | 66095-81-6 |
| HC Orange No. 2 | orange | 85765-48-6 |
| HC Orange No. 3 | orange | 81612-54-6 |
| HC Blue No. 2 | blue | 33229-34-4 |
| HC Blue No. 12 | blue | 132885-85-9 |
| HC Blue No. 10 | blue | 173994-75-7 |
| HC Blue No. 9 | blue | 114087-42-2 |
| Indigo | blue | 482-89-3 |
| HC Blue No. 14 | blue | 99788-75-7 |
| Disperse Blue 23 | blue | 4471-41-4 |
| Disperse Blue 3 | blue | 2475-46-9 |
| Disperse Blue 377 | blue | 67674-26-4 |
| HC Green No. 1 | green | 52136-25-1 |
| 1,2,3,4-tetrahydro-6-nitrochinoxalin | brown | 41959-35-7 |
| Disperse Black 9 | black | 20721-50-0 |

| Preferred Nonionic Direct Dyes | | |
|---|---|---|
| 2-amino-6-chloro-4-nitrophenol | red | 6358-09-4 |
| HC Red 3 | red | 2871-01-4 |
| 4-nitro-o-phenylenediamine | orange-red | 99-56-9 |
| Disperse Violet 1 | violet | 128-95-0 |
| HC Yellow 2 | yellow | 4926-55-0 |
| HC Yellow 4 | yellow | 59820-43-8 |
| HC Yellow 15 | yellow | 138377-66-9 |
| HC Blue 2 | blue | 33229-34-4 |
| Disperse Blue 3 | blue | 2475-46-9 |
| Disperse Blue 377 | blue | 67674-26-4 |
| Disperse Black 9 | black | 20721-50-0 |

Carbonate Ion Source

Optionally the soluble solid hair coloring article may comprise a source of carbonate ions or carbamate ions or hydrogencarbonate ions or peroxymonocarbonate ions or any mixture thereof. The carbonate ions or carbamate ions or hydrogencarbonate ions or peroxymonocarbonate ions may be contained by the porous solid in the sense that the porous solid forms a holding container for the carbonate ions or carbamate ions or hydrogencarbonate ions or peroxymonocarbonate ions. Alternatively, the carbonate ions or carbamate ions or hydrogencarbonate ions or peroxymonocarbonate ions may be incorporated as part of the processing mixture used to form the porous solid. The carbonate ions or carbamate ions or hydrogencarbonate ions or peroxymonocarbonate ions may be located with the direct dye and any other optional materials (e.g., oxidizing agents) or isolated from these materials.

The source of said ions herein is provided in the composition to provide a carbonate ion concentration of at least 0.2 mol/L upon admixture of the soluble solid hair coloring article with water. The soluble solid hair coloring article are designed to preferably provide from about 0.4 mol/l to about 2.0 mol/L, more preferably from about 0.5 mol/L to about 1.5 mol/L of the source of said ions, upon admixture of the soluble solid hair coloring article with water.

Any source of these ions may be utilized, including solid sources. Suitable sources for use herein include sodium, potassium, lithium, calcium, magnesium, barium, ammonium salts of carbonate, carbamate and hydrogencarbonate ions and mixtures thereof such as sodium carbonate, sodium hydrogen carbonate, potassium carbonate, potassium hydrogen carbonate, lithium carbonate, calcium carbonate, magnesium carbonate, barium carbonate, ammonium carbonate, ammonium hydrogen carbonate and mixtures thereof. Percarbonate salts may also be utilized to provide both the source of carbonate ions and oxidizing agent. Preferred solid sources of carbonate ions, carbamate and hydrogencarbonate ions are sodium percarbonate, potassium percarbonate, calcium percarbonate, and mixtures thereof.

Oxidizing Agent

The soluble solid hair coloring article according to the present invention may comprise at least one source of an oxidizing agent. Preferred oxidizing agents for use herein are solid water-soluble peroxygen oxidizing agents. "Water-soluble" as defined herein means that in standard condition at least 0.1 g, preferably 1 g, more preferably 10 g of said oxidizing agent can be dissolved in 1 liter of deionized water. The oxidizing agents are valuable for the initial solubilisation and decolorisation of the melanin (bleaching) in the hair shaft.

The oxidizing agents may be contained by the porous solid in the sense that the porous solid forms a holding container for the oxidizing agents. Alternatively, the oxidizing agents may be incorporated as part of the processing mixture used to form the porous solid. The oxidizing agent may be located with the direct dye, the carbonate ions or carbamate ions or hydrogencarbonate ions or peroxymonocarbonate ions or isolated from these other materials.

Any solid oxidizing agent known in the art may be utilized in the present invention. Preferred water-soluble oxidizing agents are inorganic peroxygen materials capable of yielding hydrogen peroxide in an aqueous solution. Water-soluble peroxygen oxidizing agents are well known in the art and include hydrogen peroxide, inorganic alkali metal peroxides such as sodium periodate and sodium peroxide and organic peroxides such as urea peroxide, melamine peroxide, and inorganic perhydrate salt bleaching compounds, such as the alkali metal salts of perborates, percarbonates, perphosphates, persilicates, persulphates and the like. These inorganic perhydrate salts may be incorporated as monohydrates, tetrahydrates etc. Alkyl and aryl peroxides, and/or peroxidases may also be used. Mixtures of two or more such oxidizing agents can be used if desired. Preferred for use in the soluble solid hair coloring article are percarbonate (which may be used to provide a source of both oxidizing agent and carbonate ions), persulphates and combinations thereof.

Optionally the soluble solid hair coloring article may form peroxymonocarbonate ions. These ions are typically formed in-situ from the reaction between a source of hydrogen peroxide and carbonate ion.

According to the present invention the soluble solid hair coloring article may be designed to provide from about 0.1% to about 10% by weight, in another embodiment from about 1% to about 7% by weight, and in an alternate embodiment from about 2% to about 5% by weight, of an oxidizing agent upon admixture of the soluble solid hair coloring article with water.

Source of Ammonium Ions

Optionally the soluble solid hair coloring article may comprise at least one solid source of ammonium ions. The source of the ammonium ions may be contained by the porous solid in the sense that the porous solid forms a holding container for the source of ammonium ions. Suitable holding container forms include an envelope, pouch or sandwich structure. Alternatively, the source of ammonium ions may be incorporated as part of the processing mixture used to form the porous solid.

Any solid source of ammonium ions is suitable for use herein. Preferred sources include ammonium chloride, ammonium sulphate, ammonium nitrate, ammonium phosphate, ammonium acetate, ammonium carbonate, ammonium hydrogen carbonate, ammonium carbamate, ammonium hydroxide, percarbonate salts, ammonia and mixtures thereof. Particularly preferred are ammonium sulfate, ammonium carbonate, ammonium carbamate, ammonia and mixtures thereof. In one embodiment, the source of ammonium ions and source of carbonate ions or carbamate ions or hydrogencarbonate ions or peroxymonocarbonate ions or any mixture thereof, are present in the soluble solid hair coloring article at a weight ratio of from 3:1 to 1:10, preferably 2:1 to 1:5.

The soluble solid hair coloring articles are preferably designed to provide from about 0.1% to about 10% by weight, alternatively from about 0.5% to about 5% by weight, and alternatively from about 1% to about 3% by weight, of ammonium ions upon admixture of the soluble solid hair coloring article with water.

Water-Soluble Polymer ("Polymer Structurant")

The present invention comprises water-soluble polymer that functions as a structurant. As used herein, the term "water-soluble polymer" is broad enough to include both water-soluble and water-dispersible polymers, and is defined as a polymer with solubility in water, measured at 25° C., of at least about 0.1 gram/liter (g/L). In some embodiments, the polymers have solubility in water, measured at 25° C., of from about 0.1 gram/liter (g/L) to about 500 grams/liter (g/L). This level indicates production of a macroscopically isotropic or transparent, colored or colorless solution. The polymers for making these solids may be of synthetic or natural origin and may be modified by means of chemical reactions. They may or may not be film-forming. These polymers should be physiologically acceptable, i.e., they should be compatible with the skin, mucous membranes, the hair and the scalp.

The terms "water-soluble polymer" and "polymer structurant" are used interchangeably herein. Furthermore, whenever the singular term "polymer" is stated, it should be understood that the term is broad enough to include one polymer or a mixture of more than one polymer. For instance, if a mixture of polymers is used, the polymer solubility as referred to herein would refer to the solubility of the mixture of polymers, rather than to the solubility of each polymer individually.

The one or more water-soluble polymers of the present invention are selected such that their weighted weight average molecular weight is from about 40,000 to about 500,000, in one embodiment from about 50,000 to about 400,000, in yet another embodiment from about 60,000 to about 300,000, and in still another embodiment from about 70,000 to about 200,000. The weighted weight average molecular weight is computed by summing the weight average molecular weights of each polymer raw material multiplied by their respective relative weight percentages by weight of the total weight of polymers present within the porous solid. Suitable water-soluble polymers are discussed in WO 2010077650 A2 at page 19, line 26-page 22, line 12.

The water-soluble polymer may be present from about 10% to about 50% by weight of the porous dissolvable solid substrate of one or more water-soluble polymer, in one embodiment from about 15% to about 40%, and in a particular embodiment from about 20% to about 30% by weight of the porous dissolvable solid substrate of one or more water-soluble polymers.

The water-soluble polymer may be present from about 10% to about 50% by weight of the pre-mix used to form the porous dissolvable solid substrate of one or more water-soluble polymer, in one embodiment from about 10% to about 20%, and in another embodiment from about 10% to about 15%, by weight.

Water-soluble polymers of the present invention include polyvinyl alcohols, polyvinylpyrrolidones, starch and starch derivatives, pullulan, gelatin, hydroxypropylmethylcelluloses, methycelluloses, and carboxymethycelluloses.

Water-soluble polymers of the present invention include polyvinyl alcohols, and hydroxypropylmethylcelluloses. Suitable polyvinyl alcohols include those available from Celanese Corporation (Dallas, Tex.) under the Celvol trade name including, but not limited to, Celvol 523, Celvol 530, Celvol 540, Celvol 518, Celvol, 513, Celvol 508, Celvol 504, and combinations thereof. Suitable hydroxypropylmethylcelluloses include those available from the Dow Chemical Company (Midland, Mich.) under the Methocel trade name including, but not limited, to Methocel E50, Methocel E15, Methocel E6, Methocel ES, Methocel E3, Methocel F50, Methocel K100, Methocel K3, Methocel A400, and combinations thereof including combinations with above mentioned hydroxypropylmethylcelluloses.

In one embodiment polyvinyl chloride is a suitable polymer structurant.

Polymeric Structurant Additive

The porous solid of the soluble solid hair coloring article may comprise an additive that aids in processing, provides sensory benefits, or both. Such additives include polyalkylene oxides selected such that their approximate weight average molecular weight is between about 100,000 and about 4,000,000. The additive may provide foam boosting properties and may also act as an emollient, providing benefits to both the manufacture of the porous solid and end use benefits to the hair after application of the hair coloring article. Suitable additives may be selected from materials from Dow Chemical sold under the tradename POLYOX™ ex. the Dow Chemical Company or an affiliated company of Dow.

| POLYOX Grades | INCI Name | Approx. Molecular Weight | Viscosity (cPs) |
|---|---|---|---|
| POLYOX WSR-205 | PEG-14M | 600,000 | 4500-8800[a] |
| POLYOX WSR-301 | PEG-90M | 4,000,000 | 1650-5500[c] |
| POLYOX WSR N-10 | PEG-2M | 100,000 | 12-50[a] |
| POLYOX WSR N-80 | PEG-5M | 200,000 | 65-115[a] |
| POLYOX WSR N-750 | PEG-7M | 300,000 | 600-1,000[a] |
| POLYOX WSR N-3000 | PEG-14M | 400,000 | 2250-4500[a] |
| POLYOX WSR N-12K | PEG-23M | 1,000,000 | 400-800[b] |
| POLYOX WSR N-60K | PEG-45M | 2,000,000 | 200-400[b] |

[a]5% solution
[b]2% solution
[c]1% solution

The polymeric structurant additive may be present in the soluble solid hair coloring article, such as the porous solid, from about 0.1% to about 10% by weight of the premix that is formed into the porous solid, such as from about 1% to about 8%, such as from about 2% to about 5% by weight of the premix that is formed into the porous solid.

Plasticizer

The porous solid of the soluble solid hair coloring article comprises a water soluble plasticizing agent suitable for use in the soluble hair coloring article. Non-limiting examples of suitable plasticizing agents include polyols, copolyols, polycarboxylic acids, polyesters and dimethicone copolyols.

In one embodiment, the one or more plasticizers may be present from about 1% to about 30% by weight of the soluble solid hair coloring article, such as the porous solid; in another embodiment from about 3% to about 25%, in another embodiment from about 5% to about 20%, and in yet another embodiment from about 8% to about 15% by weight of the soluble solid hair coloring article, such as the porous solid.

The one or more plasticizers may be present from about 1% to about 10% by weight of the premix used to form the soluble solid hair coloring article, such as the porous solid, in one embodiment from about 3% to about 6% by weight of the premix.

Examples of useful polyols include, but are not limited to, glycerin, diglycerin, propylene glycol, ethylene glycol, butylene glycol, pentylene glycol, cyclohexane dimethanol, hexane diol, polyethylene glycol (200-600), sugar alcohols such as sorbitol, manitol, lactitol and other mono- and polyhydric low molecular weight alcohols (e.g., C2-C8 alcohols); mono di- and oligo-saccharides such as fructose, glucose, sucrose, maltose, lactose, and high fructose corn syrup solids and ascorbic acid. Examples of polycarboxylic acids include, but are not limited to citric acid, maleic acid, succinic acid, polyacrylic acid, and polymaleic acid. Examples of suitable polyesters include, but are not limited to, glycerol triacetate, acetylated-monoglyceride, diethyl phthalate, triethyl citrate, tributyl citrate, acetyl triethyl citrate, acetyl tributyl citrate. Examples of suitable dimethicone copolyols include, but are not limited to, PEG-12 dimethicone, PEG/PPG-18/18 dimethicone, and PPG-12 dimethicone.

Other suitable platicizers of the present invention include, but are not limited to, alkyl and allyl phthalates; napthalates; lactates (e.g., sodium, ammonium and potassium salts); sorbeth-30; urea; lactic acid; sodium pyrrolidone carboxylic acid (PCA); sodium hyraluronate or hyaluronic acid; soluble collagen; modified protein; monosodium L-glutamate; alpha & beta hydroxyl acids such as glycolic acid, lactic acid, citric acid, maleic acid and salicylic acid; glyceryl polymethacrylate; polymeric plasticizers such as polyquaterniums; proteins and amino acids such as glutamic acid, aspartic acid, and lysine; hydrogen starch hydrolysates; other low molecular weight esters (e.g., esters of $C_2$-$C_{10}$ alcohols and acids); and any other water soluble plasticizer known to one skilled in the art of the foods and plastics industries; and mixtures thereof. EP283165B1 discloses other suitable plasticizers, including glycerol derivatives such as propoxylated glycerol.

In one embodiment, the plasticizers include glycerin or propylene glycol and combinations thereof.

Surfactants and Emulsifiers

The surfactant component of the porous solid of the soluble solid hair coloring article is used as a processing aide in preparing a stable solid porous structure for the porous solids described herein.

Anionic Surfactants

The porous solid may comprise from about 2% to about 75% of an anionic surfactant, by weight of the soluble solid hair coloring article, such as the porous solid. The anionic surfactant may be present from about 0.1% to about 30% by weight of the premix used to form the soluble solid hair coloring article, such as the porous solid of anionic surfactants, such as from about 1% to about 25% by weight of the premix used to form the porous solid of anionic surfactants.

Non limiting examples of anionic surfactants are described in U.S. Pat. Nos. 2,486,921; 2,486,922; and 2,396,278. Non-limiting examples of anionic surfactants suitable for use herein include alkyl and alkyl ether sulfates, sulfated monoglycerides, sulfonated olefins, alkyl aryl sulfonates, primary or secondary alkane sulfonates, alkyl sulfosuccinates, acyl taurates, acyl isethionates, alkyl glycerylether sulfonate, sulfonated methyl esters, sulfonated fatty acids, alkyl phosphates, acyl glutamates, acyl sarcosinates, alkyl sulfoacetates, acylated peptides, alkyl ether carboxylates, acyl lactylates, anionic fluorosurfactants, sodium lauroyl glutamate, and combinations thereof.

Anionic surfactants suitable include alkyl and alkyl ether sulfates. These materials have the respective formulae $ROSO_3M$ and $RO(C_2H_4O)_xSO_3M$, wherein R is alkyl or alkenyl of from about 8 to about 24 carbon atoms, x is 1 to 10, and M is a water-soluble cation such as ammonium, sodium, potassium and triethanolamine. The alkyl ether sulfates are typically made as condensation products of ethylene oxide and monohydric alcohol's having from about 8 to about 24 carbon atoms. Preferably, R has from about 10 to about 18 carbon atoms in both the alkyl and alkyl ether sulfates. Useful alcohols can be derived from fats, e.g., coconut oil or tallow, or can be synthetic. Lauryl alcohol and straight chain alcohol's derived from coconut oil are preferred herein. Such alcohol's are reacted with about 1 to about 10, preferably from about 3 to about 5, and especially about 3, molar proportions of ethylene oxide and the resulting mixture of molecular species having, for example, an average of 3 moles of ethylene oxide per mole of alcohol, is sulfated and neutralized. Highly preferred alkyl ether sulfates are those comprising a mixture of individual compounds, said mixture having an average alkyl chain length of from about 10 to about 16 carbon atoms and an average degree of ethoxylation of from about 1 to about 4 moles of ethylene oxide.

Non-Ionic Surfactants

The porous solid may comprise from about 2% to about 75% of a nonionic surfactant, by weight of the soluble solid hair coloring article, such as the porous solid. The porous solid may comprise from about 0.1% to about 30% by weight of the premix used to form the porous solid of nonionic surfactants, such as from about 0.5% to about 10% by weight of the premix used to form the porous solid of nonionic surfactants.

In one embodiment nonionic surfactants are surfactants to be employed as a process aid in making the soluble porous solid. Suitable nonionic surfactants include, but are not limited to, fatty alcohols, polyoxyethylenated alkyl phenols, polyoxyethylenated alcohols, polyoxyethylenated polyoxypropylene glycols, glyceryl esters of alkanoic acids, polyglyceryl esters of alkanoic acids, propylene glycol esters of alkanoic acids, sorbitol esters of alkanoic acids, polyoxyethylenated sorbitor esters of alkanoic acids, polyoxyethylene glycol esters of alkanoic acids, polyoxyethylenated alkanoic acids, alkanolamides, N-alkylpyrrolidones, alkyl glycosides, alkyl polyglucosides, alkylamine oxides, and polyoxyethylenated silicones.

Representative fatty alcohols include decyl alcohol, lauryl alcohol, myristyl alcohol, cetyl alcohol, stearyl alcohol, oleyl alcohol and mixtures thereof.

Representative polyoxyethylenated alcohols include alkyl chains ranging in the $C_9$-$C_{16}$ range and having from about 1 to about 110 alkoxy groups including, but not limited to, laureth-3, laureth-23, ceteth-10, steareth-10, steareth-100, beheneth-10, and commercially available from Shell Chemicals, Houston, Tex. under the trade names NEODOL® 91, NEODOL® 23, NEODOL® 25, NEODOL® 45, NEODOL® 135, NEODOL® 67, NEODOL® PC 100, NEODOL® PC 200, NEODOL® PC 600, and mixtures thereof.

Also available commercially are the polyoxyethylene fatty ethers available commercially under the BRIJ® trade name from Uniqema, Wilmington, Del., including, but not limited to, BRIJ® 30, BRIJ® 35, BRIJ® 52, BRIJ® 56, BRIJ® 58, BRIJ® 72, BRIJ® 76, BRIJ® 78, BRIJ® 93, BRIJ® 97, BRIJ® 98, BRIJ® 721 and mixtures thereof.

Suitable alkyl glycosides and alkyl polyglucosides can be represented by the formula (Sugar)n-O—R wherein (Sugar) is a sugar moiety such as glucose, fructose, mannose, galactose, and the like; n is an integer of from about 1 to about 1000, and R is a $C_8$-$C_{30}$ alkyl group. Examples of long chain alcohols from which the alkyl group can be derived include decyl alcohol, lauryl alcohol, myristyl alcohol, cetyl alcohol, stearyl alcohol, oleyl alcohol, and the like. Examples of these surfactants include alkyl polyglucosides wherein (Sugar) is a glucose moiety, R is a $C_{8-20}$ alkyl group, and n is an integer of from about 1 to about 9. Commercially available examples of these surfactants include decyl polyglucoside and lauryl polyglucoside available under trade names APG® 325 CS, APG® 600 CS and APG® 625 CS) from Cognis, Ambler, Pa. Also useful herein are sucrose ester surfactants such as sucrose cocoate and sucrose laurate and alkyl polyglucosides available under trade names TRITON™ BG-10 and TRITON™ CG-110 from The Dow Chemical Company, Houston, Tex.

Other nonionic surfactants suitable for use in the present invention are glyceryl esters and polyglyceryl esters, including but not limited to, glyceryl monoesters, glyceryl monoesters of $C_{12-22}$ saturated, unsaturated and branched chain fatty acids such as glyceryl oleate, glyceryl monostearate, glyceryl monopalmitate, glyceryl monobehenate, and mixtures thereof, and polyglyceryl esters of $C_{12-22}$ saturated, unsaturated and branched chain fatty acids, such as polyglyceryl-4 isostearate, polyglyceryl-3 oleate, polyglyceryl-2-sesquioleate, triglyceryl diisostearate, diglyceryl monooleate, tetraglyceryl monooleate, and mixtures thereof.

Also useful herein as nonionic surfactants are sorbitan esters. Sorbitan esters of $C_{12-22}$ saturated, unsaturated, and branched chain fatty acids are useful herein. These sorbitan esters usually comprise mixtures of mono-, di-, tri-, etc. esters. Representative examples of suitable sorbitan esters include sorbitan monolaurate (SPAN® 20), sorbitan monopalmitate (SPAN® 40), sorbitan monostearate (SPAN® 60), sorbitan tristearate (SPAN® 65), sorbitan monooleate (SPAN® 80), sorbitan trioleate (SPAN® 85), and sorbitan isostearate.

Also suitable for use herein are alkoxylated derivatives of sorbitan esters including, but not limited to, polyoxyethylene (20) sorbitan monolaurate (TWEEN® 20), polyoxyethylene (20) sorbitan monopalmitate (TWEEN® 40), polyoxyethylene (20) sorbitan monostearate (TWEEN® 60), polyoxyethylene (20) sorbitan monooleate (TWEEN® 80), polyoxyethylene (4) sorbitan monolaurate (TWEEN® 21), polyoxyethylene (4) sorbitan monostearate (TWEEN® 61), polyoxyethylene (5) sorbitan monooleate (TWEEN® 81), and mixtures thereof, all available from Uniqema.

Also suitable for use herein are alkylphenol ethoxylates including, but not limited to, nonylphenol ethoxylates (TERGITOL™ NP-4, NP-6, NP-7, NP-8, NP-9, NP-10, NP-11, NP-12, NP-13, NP-15, NP-30, NP-40, NP-50, NP-55, NP-70 available from The Dow Chemical Company, Houston, Tex.) and octylphenol ethoxylates (TRITON™ X-15, X-35, X-45, X-114, X-100, X-102, X-165, X-305, X-405, X-705 available from The Dow Chemical Company, Houston, Tex.).

Also suitable for use herein are alkanolamides including cocamide monoethanolamine (CMEA) and tertiary alkylamine oxides including lauramine oxide and cocamine oxide.

In one embodiment a mixture of nonionic and anionic surfactant are present from about 2% to about 75% by weight of the soluble solid hair coloring article.

Amphoteric Surfactants

The porous solid may comprise from about 2% to about 75% of an amphoteric surfactant, by weight of the soluble solid hair coloring article, such as the porous solid. The porous solid may comprise from about 0.1% to about 30% by weight of the premix used to form the porous solid of amphoteric surfactants, such as from about 1% to about 25% by weight of the premix used to form the porous solid of amphoteric surfactants.

Amphoteric surfactants suitable for use in the soluble porous solid includes those that are broadly described as derivatives of aliphatic secondary and tertiary amines in which the aliphatic radical can be straight or branched chain and wherein one of the aliphatic substituents contains from about 8 to about 18 carbon atoms and one contains an anionic water solubilizing group, e.g., carboxy, sulfonate, sulfate, phosphate, or phosphonate. Examples of compounds falling within this definition are sodium 3-dodecyl-aminopropionate, sodium 3-dodecylaminopropane sulfonate, sodium lauryl sarcosinate, N-alkyltaurines such as the one prepared by reacting dodecylamine with sodium isethionate according to the teaching of U.S. Pat. No. 2,658,072, N-higher alkyl aspartic acids such as those produced according to the teaching of U.S. Pat. No. 2,438,091, and the products described in U.S. Pat. No. 2,528,378.

Zwitterionic surfactants suitable for use include those that are broadly described as derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one contains an anionic group, e.g., carboxy, sulfonate, sulfate, phosphate, or phosphonate. Zwitterionic surfactants suitable for use include betaines, including cocoamidopropyl betaine, alkylamphoacetates including lauroamphoacetate and cocoamphoacetate. Alkylamphoacetates can be comprised of monoacetates and diacetates.

Emulsifiers

The premix for making the soluble solid hair coloring article, such as a porous solid, may comprise from about 1% to about 20% of an emulsifier, by weight of the soluble solid hair coloring article, such as the porous solid. Examples of emulsifiers include mono- and di-glycerides, polyglycerol esters, propylene glycol esters, sorbitan esters and other emulsifiers known or otherwise commonly used to stabilize air interfaces.

Optional Ingredients

The soluble solid hair coloring article, such as a porous solid, may further comprise other optional ingredients that are known for use or otherwise useful in a hair colorant composition, provided that such optional materials are compatible with the selected essential materials described herein, or do not otherwise unduly impair product performance.

Such optional ingredients are most typically those materials approved for use in cosmetics. Non limiting examples of such optional ingredients include silicones, including amino-silicones, preservatives, thickeners, sensates, plant extracts, pH modifiers, anti-microbial agents, co-solvents or other additional solvents, and similar other materials.

Silicones

An optional ingredient may include silicones, such as polyalkyl siloxanes, polyaryl siloxanes, polyalkylaryl siloxanes, polyether siloxane copolymers, amino substituted silicones, quaternized silicones, and mixtures thereof. Preferred polyalkyl siloxanes include, for example, polydimethylsiloxane, polydiethylsiloxane, and polymethylphenylsiloxane. Polydimethylsiloxane, which is also known as dimethicone, is especially preferred. Suitable amino substituted silicones include terminally substituted or pendant substituted amino substituted silicones.

Silicones may be present from about 0.5% to about 5% by weight of the premix used to form the soluble solid hair coloring article, such as a porous solid.

Suitable terminally substituted amino silicones conform to the general formula (I):

$$(R_1)_a G_{3-a}\text{-Si}-(-OSiG_2)_n-(-OSiG_b(R_1)_{2-b})_m-O-SiG_{3-a}(R_1)_a \quad \text{formula (I)}$$

wherein G of formula (I) is hydrogen, phenyl, hydroxy, or $C_1$-$C_8$ alkyl, preferably methyl; a of formula (I) is 0 or an integer having a value from 1 to 3, preferably 1; b of formula (I) is 0, 1 or 2, preferably 1; n of formula (I) is a number from 0 to 1,999; m is an integer from 0 to 1,999; the sum of n and m is a number from 1 to 2,000; a and m are not both 0; $R_1$ of formula (I) is a monovalent radical conforming to the general formula $CqH_{2q}L$, wherein q is an integer having a value from 2 to 8 and L is selected from the following groups: $-N(R_2)CH_2-CH_2-N(R_2)_2$; $-N(R_2)_2$; $-N(R_2)_3A^-$; $-N(R_2)CH_2-CH_2-NR_2H_2A^-$; wherein $R_2$ is hydrogen, phenyl, benzyl, or a saturated hydrocarbon radical, preferably an alkyl radical from about $C_1$ to about $C_{20}$; $A^-$ is a halide ion.

Highly preferred amino silicones are those corresponding to formula (I) wherein m=0, a=1, q=3, G=methyl, n is preferably from about 1500 to about 1700, more preferably about 1600; and L is $-N(CH_3)_2$ or $-NH_2$, more preferably $-NH_2$. Another highly preferred amino silicones are those corresponding to formula (I) wherein m=0, a=1, q=3, G=methyl, n is preferably from about 400 to about 600, more preferably about 500; and L is $-N(CH_3)_2$ or $-NH_2$, more preferably $-NH_2$. Such highly preferred amino silicones can be called terminal aminosilicones, as one or both ends of the silicone chain are terminated by a nitrogen containing group.

Suitable pendant substituted amino silicones are discussed in US 2007/0039103A1 at paragraphs [0027]-[0031].

Other optional ingredients include organic solvents, especially water miscible solvents and co-solvents useful as solublizing agents for polymeric structurants and as drying accelerators. Non-limiting examples of suitable solvents include alcohols, esters, ketones, aromatic hydrocarbons, aliphatic hydrocarbons, ethers, and combinations thereof. In one embodiment the alcohols are monohydric.

In another embodiment monohydric alcohols are ethanol, iso-propanol, and n-propanol. In one embodiment esters are ethyl acetate and butyl acetate. Other non-limiting examples of suitable organic solvents are benzyl alcohol, amyl acetate, propyl acetate, acetone, heptane, iso-butyl acetate, iso-propyl acetate, toluene, methyl acetate, iso-butanol, n-amyl alcohol, n-butyl alcohol, hexane, and methyl ethyl ketone. methanol, ethanol, n-propanol, isopropanol, n-butanol, isobutanol, methylethylketone, acetone, and combinations thereof.

Other optional ingredients include latex or emulsion polymers, thickeners such as water soluble polymers, clays, silicas, waxes, ethylene glycol distearate, deposition aids, including coacervate forming components and quaternary amine compounds.

Product Form

The soluble porous solids can be produced in any of a variety of product forms, including soluble porous solids that can be used alone or in combination with direct dyes and other optional components. The soluble porous solids are in the form of one or more flat sheets or pads of an adequate size to be able to be handled easily by the user. It may have a square, rectangle or disc shape or any other shape. The pads can also be in the form of a continuous strip including delivered on a tape-like roll dispenser with individual portions dispensed via perforations and/or a cutting mechanism. Alternatively, the soluble porous solids of the present invention are in the form of one or more cylindrical objects, spherical objects, tubular objects or any other shaped object. The soluble porous solids may have a thickness (caliper) of from about 0.5 mm to about 10 mm, in one embodiment from about 1 mm to about 7 mm, and in still another embodiment from about 2 mm to about 6 mm. In the case of cylindrical, spherical, or other objects with more of a third dimension versus a pad or strip, the thickness is taken as the maximum distance of the shortest dimension, i.e., the diameter of a sphere or cylinder for instance.

The soluble porous solids may comprise one or more textured, dimpled or otherwise topographically patterned surfaces including letters, logos or figures. The textured substrate can result from the shape of the substrate, in that the outermost surface of the substrate contains portions that are raised with respect to other areas of the surface. The raised portions can result from the formed shape of the article, for example the article can be formed originally in a dimpled or waffle pattern. The raised portions can also be the result of creping processes, imprinted coatings, embossing patterns, laminating to other layers having raised portions, or the result of the physical form of the soluble porous solid substrate itself. The texturing can also be the result of laminating a first soluble porous solid to a second soluble porous solid that is textured.

In a particular embodiment, the soluble porous solids may be perforated with holes or channels penetrating into or through the porous solid. These perforations can be formed during the drying process via spikes extended from the surface of the underlying mould, belt or other non-stick surface. Alternatively, these perforations can be formed after the drying process via poking or sticking the porous solids with pins, needles or other sharp objects. In one embodiment, these perforations are great in number per surface area, but not so great in number so as to sacrifice the integrity or physical appearance of the porous solid. Without being limited by a theory, it is believed that perforations increase the dissolution rate of the porous solids into water relative to un-perforated porous solids.

The soluble porous solids can also be delivered via a water insoluble implement or device. For instance, they may be attached or glued by some mechanism to an applicator to facilitate application to hair, i.e., a comb, rag, wand, or any other conceivable water-insoluble applicator. Additionally, the soluble porous solids may be adsorbed to the surfaces of a separate high surface area water-insoluble implement, i.e., a porous sponge, a puff, a flat sheet etc. For the latter, the soluble porous solid may be adsorbed as a thin film or layer or included within a specific regional space provided by the implement.

Method of Manufacture

The soluble solid hair coloring article comprises a soluble porous solid which can be prepared by the process comprising: (1) Preparing a processing mixture comprising surfactant(s), dissolved polymer structurant and other optional ingredients; (2) Aerating the processing mixture by introducing a gas into the mixture to form an aerated processing mixture; (3) Forming the aerated process mixture into one or more desired shapes to form a shaped aerated processing mixture; and (4) Drying the shaped aerated processing mixture to a desired final moisture content (e.g., from about 0.1% to about 25%, in one embodiment from about 3% to about 25%, in another embodiment from about 5% to about 20% and in yet another embodiment from about 7% to about 15%, by addition of energy) to form the soluble porous solid.

Preparation of Processing Mixture (Pre-Mix)

The processing mixture or pre-mix is generally prepared by dissolving the polymer structurant in the presence of water, plasticizer and other optional ingredients by heating followed by optional cooling. In one embodiment, a direct dye is included in the preparation step with the surfactant(s), dissolving polymer structurant and plasticizer. The preparation step is accomplished by dissolving the desired components in any suitable heated batch agitation system or via any suitable continuous system involving either single screw or twin screw extrusion or heat exchangers together with either high shear or static mixing. The ingredients may be included in a step-wise via pre-mix portions or of any combination of ingredients or as a single batch.

The processing mixtures may comprise: from about 15% to about 50% solids, in one embodiment from about 20% to about 40% solids, and in another embodiment from about 25% to about 35% solids, by weight of the processing mixture before drying; and have a viscosity of from about 2,500 cps to about 75,000 cps, in one embodiment from about 5,000 cps to about 75,000 cps, in another embodiment from about 7,500 cps to about 75,000 cps, and in still another embodiment from about 10,000 cps to about 75,000 cps, in another embodiment from about 65,000 cps to about 70,000 cps.

The processing mixture viscosity values can be measured on a suitable rheometer, such as a TA Instruments AR500 Rheometer with 4.0 cm diameter parallel plate and 1,200 micron gap at a shear rate of 1.0 reciprocal seconds for a period of 30 seconds at 25° C. (available from TA Instruments, New Castle, Del.), or on a standard viscometer, such as a Brookfield Model DV-1 PRIME Digital Viscometer with CP-41 and CP-42 spindles at a shear rate of 1.0 reciprocal seconds for a period of 2 minutes at 25° C. (available from Brookfield Engineering Laboratories, Inc., Middleboro, Mass.).

The percent (%) solids content is the summation of the weight percentages by weight of the total processing mixture of all of the solid, semi-solid and liquid components excluding water and any obviously volatile materials such as low boiling alcohols.

Aeration of Processing Mixture

The aeration of the processing mixture is accomplished by introducing a gas into the mixture, in one embodiment by mechanical mixing energy but also may be achieved via other physical or chemical means. The aeration may be accomplished by any suitable mechanical processing means, including but not limited to: (i) Batch tank aeration via mechanical mixing including planetary mixers or other suitable mixing vessels, (ii) semi-continuous or continuous aerators utilized in the food industry (pressurized and non-pressurized), (iii) gas injection, (iv) gas evolution via a pressure drop, or (v) spray-drying the processing mixture in order to form aerated beads or particles that can be compressed such as in a mould with heat.

In a particular embodiment, it has been discovered that the soluble porous solids of the present invention can be prepared within semi-continuous and continuous pressurized aerators that are conventionally utilized within the foods industry in the production of marshmallows. Suitable pressurized aerators include the Morton whisk (Morton Machine Co., Motherwell, Scotland), the Oakes continuous automatic mixer (E. T. Oakes Corporation, Hauppauge, N.Y.), the Fedco Continuous Mixer (The Peerless Group, Sidney, Ohio), and the Preswhip (Hosokawa Micron Group, Osaka, Japan).

Forming the Aerated Processing Mixture

The forming of the aerated processing mixture may be accomplished by any suitable means to form the aerated processing mixture in a desired shape or shapes including, but not limited to (i) depositing the aerated processing mixture to specially designed moulds comprising a non-interacting and non-stick surface including TEFLON®, metal, HDPE, polycarbonate, neoprene, rubber, LDPE, glass and the like; (ii) depositing the aerated processing mixture into cavities imprinted in dry granular starch contained in a shallow tray (starch moulding forming technique widely utilized in the confectionery industry); or (iii) depositing the aerated processing mixture onto a continuous belt or screen comprising any non-interacting or non-stick material such as TEFLON®, metal, HDPE, polycarbonate, neoprene, rubber, LDPE, glass and the like to form a shaped aerated processing mixture. Optionally, stamping, cutting or embossment of the shaped aerated processing mixture may occur.

Drying the Shaped Aerated Processing Mixture

The drying of the shaped aerated processing mixture may be accomplished by any suitable means including, but not limited to: (i) drying room(s) including rooms with controlled temperature and pressure or atmospheric conditions; (ii) ovens including non-convection or convection ovens with controlled temperature and optionally humidity; (iii) Truck/Tray driers, (iv) multi-stage inline driers; (v) impingement ovens; (vi) rotary ovens/driers; (vii) inline roasters; (viii) rapid high heat transfer ovens and driers; (ix) dual plenum roasters, (x) conveyor driers, (xi) microwave drying technology, and combinations thereof. Any suitable drying means that does not comprise freeze-drying can be used to form the soluble porous solid. If continuous shaping processes are used, the resulting soluble porous solid may be stamped, cut, embossed and/or stored in roll form.

Optional ingredients may be imparted during any of the above described four processing steps or even after the drying process.

The soluble porous solids of the present invention may also be prepared with chemical foaming agents by in-situ gas formation (via chemical reaction of one or more ingredients, including formation of $CO_2$ by an effervescent system).

Performance and Physical Characteristics

Dissolution Rate

The soluble porous solid may have a Dissolution Rate that allows the porous solid to rapidly disintegrate during use with the application with water. The Dissolution Rate of the soluble porous solid component is determined in accordance with the methodology described below.

Hand Dissolution Method: Approximately 0.5 g of the soluble porous solid is placed in the palm of the hand while wearing nitrile gloves. 7.5 cm³ of luke warm tap water (from about 30° C. to about 35° C.) is quickly applied to the product via syringe. Using a circular motion, palms of hands are rubbed together 2 strokes at a time until dissolution occurs (up to 30 strokes). The hand dissolution value is reported as the number of strokes it takes for complete dissolution or as 30 strokes as the maximum (in the case for where the solid is considered non-dissolving).

The soluble porous solids have a hand dissolution value of from about 1 to about 30 strokes, in one embodiment from about 2 to about 25 strokes, in another embodiment from about 3 to about 20 strokes, and in still another embodiment from about 4 to about 15 strokes.

Thickness

In one embodiment the soluble porous solid may be a flat, flexible substrate in the form of a pad, a strip or tape and having a thickness of from about 0.5 mm to about 10 mm, in one embodiment from about 1 mm to about 7 mm, and in another embodiment from about 2 mm to about 6 mm, as measured by the below methodology. In the case of cylindrical, spherical, or other objects with more of a third dimension versus a pad or strip, the thickness is taken as the maximum distance of the shortest dimension, i.e., the diameter of a sphere or cylinder for instance, and the thickness ranges are the same as described above.

The thickness of the soluble porous solid (i.e., substrate or sample substrate) is obtained using a micrometer or thickness gage, such as the Mitutoyo Corporation Digital Disk Stand Micrometer Model Number IDS-1012E (Mitutoyo Corporation, 965 Corporate Blvd, Aurora, Ill., USA 60504). The micrometer has a 1 inch diameter platen weighing about 32 grams, which measures thickness at an application pressure of about 40.7 phi (6.32 gm/cm²).

The thickness of the soluble porous solid is measured by raising the platen, placing a section of the sample substrate on the stand beneath the platen, carefully lowering the platen to contact the sample substrate, releasing the platen, and measuring the thickness of the sample substrate in millimeters on the digital readout. The sample should be fully extended to all edges of the platen to make sure thickness is measured at the lowest possible surface pressure, except for the case of more rigid substrates which are not flat. For more rigid substrates which are not completely flat, a flat edge of the substrate is measured using only one portion of the platen impinging on the flat portion of the substrate.

Basis Weight

The soluble porous solid component may have a basis weight of from about 125 grams/m² to about 3,000 grams/m², in one embodiment from about 150 grams/m² to about 1,200 grams/m², in another embodiment from about 200 grams/m² to about 1,000 grams/m², and in still another embodiment from about 300 grams/m² to about 800 grams/m².

The basis weight of the soluble porous solid component is calculated as the weight of the soluble porous solid component per area of the selected soluble porous solid (grams/m²). The area is calculated as the projected area onto a flat surface perpendicular to the outer edges of the porous solid. For a flat object, the area is thus computed based on the area enclosed within the outer perimeter of the sample. For a spherical object, the area is thus computed based on the average diameter as $3.14 \times (diameter/2)^2$. For a cylindrical object, the area is thus computed based on the average diameter and average length as diameter×length. For an irregularly shaped three dimensional object, the area is computed based on the side with the largest outer dimensions projected onto a flat surface oriented perpendicularly to this side. This can be accomplished by carefully tracing the outer dimensions of the object onto a piece of graph paper with a pencil and then computing the area by approximate counting of the squares and multiplying by the known area of the squares or by taking a picture of the traced area (which can be shaded-in for contrast) including a scale and using image analysis techniques.

Density

The soluble porous solid can be characterized in terms of a density determination. The density of the soluble porous solid is determined by the equation: Calculated Density=Basis Weight of porous solid/(Porous Solid Thickness×1,000), wherein the porous solid has a density of from about 0.03 g/cm³ to about 0.4 g/cm³, in one embodiment from about 0.05 g/cm³ to about 0.3 g/cm³, and in another embodiment from about 0.075 g/cm³ to about 0.2 g/cm³. The Basis Weight and Thickness of the soluble porous solid are determined in accordance with the methodologies described herein.

Figure 2:
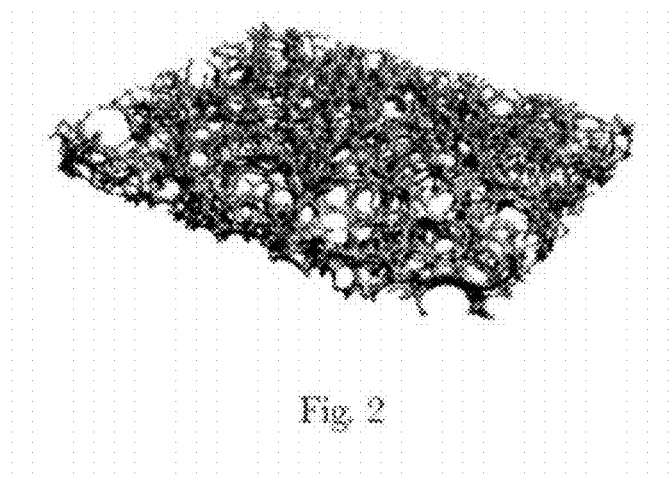
FIG. 2 is a micro computed tomography system image of a soluble porous solid having a density of 0.08 grams/cm$^3$ (with 60 seconds of mixing)

FIGS. 1-3 exemplify desired densities herein rather than higher densities that can be exemplified in comparative densities in FIGS. 4-5.

Cell Inter-Connectivity

The soluble porous solids with the above mentioned characteristics have a high degree of cell inter-connectivity, i.e., are predominantly open-celled solid foams as opposed to being predominantly closed-cell solid foams. The cell inter-connectivity can be assessed by cutting a 2-3 mm wide sliver of the solid in the z-direction using scissors or a sharp blade, measured across the normal x-y largest surface of the solid, and turning the resulting sliver by 90 degrees to reveal the internal cellular structure of the freshly cut cross-sectional area. This cross-sectional area can be assessed by close visual inspection or, more accurately, by employing magnification under a stereo microscope such as the SZX12 Stereo microscope available from Olympus Olympus America Inc., Center Valley, Pa. The open-celled soluble porous solids can easily be identified by examining the inner portion of the cross-sectional area which will comprise a predominantly three dimensional network of struts with open void spaces surrounding the struts that are inter-connected to one another including in the third dimension through the depth of the cross-section. In contrast, the inner cross-section of a closed-cell foam will appear as discrete bubbles that are cut across and then only being inter-connected at the cross-sectional surface in two dimensions by virtue of the cutting process employed to generate the exposed cross-sectional area.

Solid Flexibility and Cohesiveness

The physical integrity of the soluble porous solids (or solid cohesiveness) is assessed via a qualitative rating system by two separate qualitative ratings (1 to 4 scale) on brittleness/flexibility (brittle is breakable) and cohesiveness (ease in removing from moulds):

| Brittleness/Flexibity Qualitative Rating | | | |
|---|---|---|---|
| Very brittle = 1 | Somewhat brittle = 2 | Somewhat flexible = 3 | Very flexible = 4 |

| Cohesiveness Qualitative Rating (Ease of removal from moulds) | | | |
|---|---|---|---|
| Very difficult = 1 | Somewhat difficult = 2 | Somewhat easy = 3 | Very easy = 4 |

These ratings are assessed on three dimensional moulds and resulting flat solids with z-dimension thicknesses between 3 mm and 10 mm and extending in the x-y dimensions encompassing surface areas of between 10 cm² and 60 cm² (with any x-y shape including circles, ovals, squares, rectangles etc.). The examples herein were evaluated employing circular Teflon moulds and resulting removed soluble porous solids with 4.15 cm diameters and depths of 0.7 cm. The brittleness/flexibility rating is judged by bending the soluble porous solid in pad form in half and assessing each pad on its propensity for breakage/creasing versus the pads resiliency and ability to return to the original shape. The cohesiveness rating is judged by peeling a freshly dried (after at least 20 hours at 40 degrees Celsius) soluble porous solid from the mould and noting the difficulty of removal. Solids with low cohesiveness ratings are difficult to remove from the moulds in one piece with significant adhesion to the mould surface and with significant solid remaining adhered to the mould after the solid removal process. Soluble porous solids with high cohesiveness ratings are easy to peel from the moulds in one piece and without significant solid remaining adhered to the mould after the soluble porous solid removal process.

Methods of Use

The soluble solid hair coloring article may be used for treating hair. The soluble solid hair coloring article may be used for whole head hair coloring, partial head hair coloring such as root touch up, highlights and lowlights.

The present application further covers a method of coloring hair comprising the steps of taking a soluble solid hair coloring article as described herein, preferably such that the weight ratio of direct dye to hair is about 2:1 to 5:1, such as 3:1 to 5:1, such as 4:1 and exposing the soluble solid hair coloring article to a solvent such that the soluble solid hair coloring article dissolves to form a hair coloring solution and then applying the hair coloring solution to hair. Hair color refreshing may be done at a neutral pH (pH about 7.0) while longer lasting hair coloring may be done at a pH of from about 7 to about 11, such as 10.

The exposure of the soluble solid hair coloring article may be to a solvent such as water, a solution of water and hydrogen peroxide, or a solution of water, hydrogen peroxide, and a source of ammonium ions.

The treatment steps also may further comprise working the hair coloring solution into the hair by hand or by a tool for a few minutes to ensure uniform application to all of the hair. The hair coloring solution remains on the hair while the end hair color develops for a time period of 5 to 45 minutes, such as 30 minutes. The consumer then rinses his/her hair thoroughly with tap water and allows it to dry and/or styles the hair.

EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention. All exemplified amounts are concentrations by weight of the total composition, i.e., wt/wt percentages, unless otherwise specified.

Example 1

Soluble Porous Solid Pre-Mix

TABLE 1

| Component | Wt % | Wt % | Wt % | Wt % |
|---|---|---|---|---|
| Distilled water | 23.4 | 24.3 | 13.4 | 13.4 |
| Glycerin | 2.9 | 2.0 | 2.9 | 2.0 |
| Polyvinyl alcohol[1] | 7.3 | — | 7.3 | — |
| Hydroxypropylmethyl cellulose[2] | — | 7.3 | — | 7.3 |
| Ammonium Laureth-3 sulfate (25% activity) | 40.0 | 40.0 | 40.0 | 40.0 |
| Ammonium Lauryl sulfate (25% activity) | 24.0 | 24.0 | 24.0 | 24.0 |
| Cetyl alcohol | 0.9 | 0.9 | 0.9 | 0.9 |
| Cocamide MEA | 1.5 | 1.5 | 1.5 | 1.5 |
| Anionic direct dye | — | — | 5.0 | 5.0 |
| Mixture of red:blue:yellow anionic direct dyes in 1:1:1 ratio | — | — | 5.0 | 5.0 |
| Total | 100.00 | 100.0 | | |

[1]CELVOL ® 523 available from Celanese Corporation (Dallas, Texas)
[2]METHOCEL ® E50 available from Dow Chemical Corporation (Midland, Michigan)

Add into an appropriately size clean vessel, distilled water and glycerin with stirring at 100-300 rpm to form a main mixture. Slowly add the CELVOL® 523 or METHOCEL® E50 to the main mixture in small increments using a spatula while continuing to stir. Slowly heat the mixture to 75° C. and then add the ammonium laureth-3 sulfate and ammonium lauryl sulfate. Heat the mixture to 75° C. and then add the cetyl alcohol and cocamide MEA and the optional direct dye(s) in the mixture. Heat the mixture to 85° C. while continuing to stir. Allow the resulting mixture to cool to room temperature. Adjust the final pH, as needed, to between 5.2-6.6 with citric acid or diluted sodium hydroxide. Transfer 250 grams of the above mixture into a 5 quart stainless steel bowl of a KITCHENAID® Mixer Model K5SS (available from Hobart Corporation, Troy, Ohio) and fitted with a flat beater attachment. The mixture is vigorously aerated at high speed for approximately 30-90 seconds. An aliquot of the resulting aerated mixture is then spread evenly with a spatula into a 19.4 ml circular Teflon mould (using rubber spatulas straight edge to scrape off excess foam leaving a flat smooth surface level with the top of the mould) which is weighed before and after with the wet mixture resulting in a wet foam density.

Evenly spread the remainder of the aerated mixture with a spatula into aluminum moulds (each with inner dimensions of 15.9 cm×15.9 cm×0.6 cm) bottom-lined with Bytac General Purpose film (Saint-Gobain, Paris, France). Place each mould into a 75° C. convection oven for 30 minutes.

Place the moulds into a 45° C. convection oven overnight.

Soluble Solid Hair Coloring Article

Comparative Example for Density

The following solid does not have the desired density of the present application and is included only for comparative purposes:

TABLE 2

| Component | Wt % |
|---|---|
| Distilled water | QS 100 |
| Glycerin | 1.0 |
| Polyvinyl alcohol[1] | 7.3 |
| Sodium Laureth-3 sulfate (28% activity) | 35.7 |
| Sodium Lauryl sulfate (29% activity) | 20.7 |
| Cetyl alcohol | 0.9 |
| Cocamide MEA | 1.5 |
| Tetrasodium EDTA | 0.04 |
| Sodium benzoate | 0.08 |
| Kathon CG[2] | 0.01 |

[1]CELVOL ® 523 available from Celanese Corporation (Dallas, Texas)
[2]5-chloro-2-methyl-4-isothiazolin-3-one and 2-methyl-4-isothiazoliin-3-one available from Rohm and Haas (Philadelphia, PA).

Add into an appropriately sized and cleaned vessel, the distilled water and glycerin with stifring at 100-300 rpm. Weigh the CELVOL® 523 into a suitable container and add slowly to the main mixture in small increments using a spatula while continuing to stir while avoiding the formation of visible lumps. Adjust the mixing speed to minimize foam formation. Heat the mixture slowly to 75° C. then add the sodium laureth-3 sulfate and sodium lauryl sulfate. Heat the mixture to 75° C. and add the cetyl alcohol and cocamide MEA. Heat the mixture to 85° C. while continuing to stir and then allow to cool to room temperature (35° C.). Adjust the final pH is between 5.2-6.6 with citric acid or diluted sodium hydroxide if necessary. The viscosity of the mixture should be approximately 65,000 to 75,000 cps at 1 s$^{-1}$.

Transfer 250 grams of the above mixture into a 5 quart stainless steel bowl of a KITCHENAID® Mixer Model K5SS (available from Hobart Corporation, Troy, Ohio) and fitted with a flat beater attachment. Vigorously aearate the mixture at high speed for 30 seconds. Spread a portion of the resulting aerated mixture with a spatula into 12 circular Teflon moulds with a 4.2 cm diameter and a depth of 0.6 cm which are weighed indicating an average wet foam density of approximately 0.31 grams/cm$^3$. Aerate the remaining mixture again for an additional 30 seconds for a total of 60 seconds. Spread a portion of the resulting aerated mixture with a spatula into 12 circular TEFLON® moulds with a 4.2 cm diameter and a depth of 0.6 cm which are weighed indicating an average wet foam density of approximately 0.21 grams/cm$^3$. Aerate the remaining mixture again for an additional 30 seconds for a total of 90 seconds. Spread a portion of the resulting aerated mixture with a spatula into 12 circular Teflon moulds with a 4.2 cm diameter and a depth of 0.6 cm which are weighed indicating an average wet foam density of approximately 0.19 grams/cm$^3$.

Place the segregated moulds into a 75° C. convection oven for 30 minutes and then place into a 40° C. convection oven for drying overnight. The following day, remove the resulting porous solids from the moulds with the aid of a thin spatula and tweezers. The approximate average density and basis weight are as indicated in Table 3. The estimated surfactant levels are between 50 wt % and 69 wt % and the estimated polymer level is between 20% and 27%, assuming a moisture content of between 0 wt % and 10 wt %.

TABLE 3

| | 30 seconds mixing | 60 seconds mixing | 90 seconds mixing |
|---|---|---|---|
| Density | 0.21 grams/cm$^3$ | 0.16 grams/cm$^3$ | 0.13 grams/cm$^3$ |
| Basis Weight | 1,260 grams/m$^2$ | 960 grams/m$^2$ | 780 grams/m$^2$ |

A micro computed tomography system image of the comparative example can be seen in FIGS. 4 and 5 showing the physical distinction in density between the comparative example and the claimed ranges of density for the present application (See FIGS. 1-3).

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A soluble solid hair coloring article comprising:
   (a) from about 0.4 to about 2.0 grams of anionic direct dye;
   (b) one or more soluble porous solids comprising:
      (i) from about 10% to about 50% polymeric structurant;
      (ii) from about 1% to about 30% plasticizer;
      (iii) from about 2% to about 75% of nonionic surfactant, anionic surfactant, or mixtures thereof;
   wherein the density of the one or more soluble porous solids is from about 0.03 g/cm3 to about 0.15 g/cm3.

2. The soluble solid hair coloring article of claim 1, wherein said one or more soluble porous solids encompass the anionic direct dye, and wherein the anionic direct dye is a solid.

3. The soluble solid hair coloring article of claim 1, wherein the anionic direct dye is incorporated with the said polymeric structurant, said plasticizer, and the said nonionic surfactant, anionic surfactant, or mixture thereof to form the soluble porous solid.

4. The soluble solid hair coloring article of claim 1, further comprising a source of carbonate ions, carbamate ions, hydrogencarbonate ions, peroxymonocarbonate ions, or a mixture thereof.

5. The soluble solid hair coloring article of claim 4, wherein the source of said carbonate ions is ammonium carbonate.

6. The soluble solid hair coloring article of claim 4, comprising said one or more soluble porous solids wherein the carbonate ions, carbamate ions, hydrogencarbonate ions, peroxymonocarbonate ions, or mixture thereof, are incorporated into the soluble porous solid.

7. The soluble solid hair coloring article of claim 4, comprising said one or more soluble porous solids encompassing carbonate ions, carbamate ions, hydrogencarbonate ions, peroxymonocarbonate ions, or a mixture thereof, wherein said ions are a solid.

8. The soluble solid hair coloring article of claim 1, further comprising at least one source of an oxidizing agent.

9. The soluble solid hair coloring article of claim 8, wherein the said at least one source of an oxidizing agent is selected from percarbonate, perborate, and persulphate salts, and combinations thereof.

10. The soluble solid hair coloring article of claim 1, wherein the polymeric structurant is selected from the group consisting of polyvinyl alcohols, hydroxypropylmethylcelluloses, and mixtures thereof.

11. The soluble solid hair coloring article of claim 1, wherein said plasticizer is selected from the group consisting of glycerin, diglycerin, propylene glycol, ethylene glycol, butylene glycol, pentylene glycol, cyclohexane dimethanol, hexane diol, polyethylene glycol, sugar alcohols; mono-di- and oligo-saccharides, ascorbic acid, and mixtures thereof.

12. The soluble solid hair coloring article of claim 1, wherein the nonionic surfactant is selected from the group consisting of sorbitan esters, alkoxylated derivatives of sorbitan esters, and mixtures thereof.

13. The soluble solid hair coloring article of claim 1, wherein the anionic surfactant is selected from the group consisting of alkyl and alkyl ether sulfates, sulfated monoglycerides, sulfonated olefins, alkyl aryl sulfonates, primary or secondary alkane sulfonates, alkyl sulfosuccinates, acyl taurates, acyl isethionates, alkyl glycerylether sulfonate, sulfonated methyl esters, sulfonated fatty acids, alkyl phosphates, acyl glutamates, acyl sarcosinates, alkyl sulfoacetates, acylated peptides, alkyl ether carboxylates, acyl lactylates, anionic fluorosurfactants, sodium lauroyl glutamate, and combinations thereof.

14. A premix for forming a soluble solid hair coloring article comprising: from about 0.4 to about 2.0 grams of anionic direct dye; polymeric structurant; plasticizer; nonionic surfactant, anionic surfactant, or a mixture thereof; and from about 50% to about 75% by weight of the premix of water.

15. The premix of claim 14, wherein the polymeric structurant is selected from the group consisting of polyvinyl alcohols, hydroxypropylmethylcelluloses, and mixtures thereof.

16. The premix of claim 14, wherein the plasticizer is selected from the group consisting of glycerin, diglycerin, propylene glycol, ethylene glycol, butylene glycol, pentylene glycol, cyclohexane dimethanol, hexane diol, polyethylene glycol, sugar alcohols; mono-, di- and oligo-saccharides; ascorbic acid; and mixtures thereof.

17. The premix of claim 14, wherein the nonionic surfactant is selected from the group consisting of sorbitan esters, alkoxylated derivatives of sorbitan esters, and mixtures thereof.

18. The premix of claim 14, wherein the anionic surfactant is selected from the group consisting of alkyl sulfates, alkyl ether sulfates, and mixtures thereof.

19. A method of coloring hair comprising the steps of:
   (a) exposing a soluble solid hair coloring article comprising anionic direct dye and one or more soluble porous solids, to a solvent such that the soluble solid hair coloring article dissolves to form a hair coloring solution; wherein the density of the one or more soluble porous solids is from about 0.03 $g/cm^3$ to about 0.15 $g/cm^3$; and further wherein the ratio of anionic direct dye to hair is from 2:1 to 5:1; and
   (b) applying the hair coloring solution to hair.

20. The method of claim 19, wherein the applying step is performed by hand or by a device.

21. The method of claim 19, wherein the method further includes the step of waiting for a period of time of from about 5 to about 45 minutes.

* * * * *